United States Patent [19]

Beshouri et al.

[11] Patent Number: 5,306,831
[45] Date of Patent: Apr. 26, 1994

[54] SORBITAN ESTER PURIFICATION PROCESS

[75] Inventors: Sharon M. Beshouri, Houston; Robert P. Adamski, Missouri City, both of Tex.

[73] Assignee: Shell Oil Company, Houston, Tex.

[21] Appl. No.: 961,241

[22] Filed: Oct. 15, 1992

[51] Int. Cl.$^5$ ............................................. C07D 307/20
[52] U.S. Cl. ...................................................... 549/478
[58] Field of Search ........................................... 549/478

[56] References Cited

U.S. PATENT DOCUMENTS

| | | | |
|---|---|---|---|
| 2,322,820 | 6/1943 | Brown | 260/345 |
| 2,997,492 | 8/1961 | Martin | 260/410.6 |
| 3,351,434 | 11/1967 | Grimes et al. | 23/310 |
| 3,579,547 | 8/1971 | Traxler | 260/410.6 |
| 3,754,377 | 8/1973 | Clonts | 55/73 |
| 3,758,404 | 9/1973 | Clonts | 208/263 |
| 3,839,487 | 10/1974 | Clonts | 260/683.48 |
| 4,297,290 | 10/1981 | Stockburger | 260/410.6 |
| 4,435,586 | 3/1984 | Kruse et al. | 549/464 |
| 4,789,468 | 12/1988 | Sirkar | 210/137 |
| 4,921,612 | 5/1990 | Sirkar | 210/644 |
| 4,997,569 | 3/1991 | Sirkar | 210/637 |
| 5,053,132 | 10/1991 | Sirkar | 210/500.23 |

OTHER PUBLICATIONS

Ault, Addison, Techniques And Experiments For Organic Chemistry, Chemistry, Organic-Laboratory Manuals, Allyn and Bacon, Inc., (Nov. 1979) Section 13, pp. 76–83.

R. Prasad and K. K. Sirkar, "Dispersion-Free Solvent Extraction With Microporous Hollow-Fiber Modules," AiChe J. 34(2), 177 (1988).

Primary Examiner—C. Warren Ivy
Assistant Examiner—Ba K. Trinh

[57] ABSTRACT

Polyol impurities in a sorbitan ester mixture is removed by treating a polyol-containing sorbitan ester dissolved in a solution containing a hydrocarbon and a polar organic solvent with an aqueous metal halide salt solution.

20 Claims, No Drawings

SORBITAN ESTER PURIFICATION PROCESS

FIELD OF THE INVENTION

This invention relates to the purification of sorbitan esters. In one aspect, the invention relates to removal of impurities from sorbitan esters

BACKGROUND OF THE INVENTION

Sorbitan fatty acid esters have wide spread utility in many areas as an emulsifying agent in the formation of water-in-oil and oil-in-water emulsions. They are readily available commercially as SPAN ® emulsifying agents and ALKAMULS ® sorbitan esters.

Sorbitan esters can be manufactured by processes described in U.S. Pat. No. 2,322,820. Generally, sorbitol and a fatty acid, or a combination of fatty acids are reacted at a temperature greater than about 200° C. under a flow of inert gas, in the presence of an acidic or basic catalyst, to produce sorbitan fatty acid esters. A combination of mono-, di-, tri-, and tetra-esters of sorbitan as well as impurities such as polyols formed by the self-condensation of sorbitan molecules, unreacted sorbitans and isosorbides are produced from this process. These impurities are also present in the commercial sorbitan esters.

It has been found that these polyol impurities tend to form undesirable sludge during emulsifying processes. Therefore, it is desirable to remove these impurities from the sorbitan fatty acid esters in order to avoid the formation of sludge.

It is therefore an object of the present invention to provide a process to purify sorbitan esters containing polyol impurities.

SUMMARY OF THE INVENTION

According to the invention, a process for removing polyols from a polyol-containing sorbitan ester mixture is provided comprising the steps of:

a) dissolving the polyol-containing sorbitan ester mixture in a solution comprising at least one hydrocarbon and at least one polar organic solvent to produce a sorbitan ester solution;

b) adding and mixing into the sorbitan ester solution, a metal salt solution comprising water and a metal salt to produce a combined solution, c) phase separating the combined solution into an organic phase comprising the hydrocarbon, polar organic solvent and sorbitan ester and an aqueous phase comprising water, metal salt and polyol, d) separating the aqueous phase from the organic phase; and e) then recovering the thus-treated sorbitan ester from the organic phase.

In another embodiment, a process for removing polyols from a polyol-containing sorbitan ester mixture is provided comprising the steps of:

a) dissolving the polyol-containing sorbitan ester mixture in a solution comprising at least one hydrocarbon and a polar organic solvent to produce a sorbitan ester solution;

b) providing a metal salt solution comprising water and a metal salt, c) contacting the sorbitan ester solution and metal salt solution under conditions effective to extract the polyols from the sorbitan ester solution, d) separating the thus treated-sorbitan ester solution and the metal salt solution, and e) then recovering the sorbitan ester from the separated-sorbitan ester solution.

DETAILED DESCRIPTION OF THE INVENTION

It has been found that polyol impurities in a sorbitan ester mixture can be removed by treating a commercial or any other synthesized sorbitan ester mixture dissolved in a hydrocarbon/polar organic solvent solution with an aqueous metal salt solution. Sorbitan esters can be mono-, di-, tri-, tetra-esters of sorbitan or mixtures thereof, sorbitan being $C_6H_8O(OH)_4$. Polyols include self-condensed and unreacted sorbitans and isosorbides.

Suitable hydrocarbons are $C_{5-20}$ straight or branched alkanes, $C_{5-20}$ cycloalkanes and $C_{6-20}$ aromatics optionally substituted with inert substituents. Inert substituents are substituents which do not react with either polyols or sorbitan esters such as, for example, alkyl and halo. Examples of such hydrocarbons include, for example, pentane, hexane, heptane, octane, decane, hexadecane, cyclohexane, toluene, ethyl benzene and petroleum ether. The preferred hydrocarbons are pentanes, hexanes, cyclohexane and petroleum ether.

Suitable polar organic solvents include oxygenated hydrocarbons such as straight, branched, cyclic or aromatic $C_1$–$C_{11}$ alcohols, aldehydes, ketones, esters and ethers: and nitrogen bases having a pKa value for their conjugate acids of less than about 10, preferably less than about 8. Examples of such alcohols include, for example, methanol, ethanol, n-propanol, isopropanol, butanol, pentanol, hexanol, cyclohexanol, benzyl alcohol and decanol. Examples of such aldehydes include, for example, formaldehyde, acetaldehyde and benzaldehyde. Examples of such ketones include, for example, acetone, methyl ethyl ketone, methyl phenyl ketone, and diethyl ketone. Examples of such esters include, for example, ethyl acetate, methyl isobutyrate and 2-ethylhexyl acrylate. Examples of such ethers include, for example, diethyl ether, dioxane and tetrahydrofuran. Examples of such nitrogen bases include, for example, acetonitrile, aniline, allyl amide and pyridine. Other suitable polar organic solvents include inert sulfur-containing solvents that do not react with polyols or sorbitan esters such as, for example, dimethyl sulfoxide and tetramethylene sulfone $C_1$–$C_5$ alcohols, particularly isopropanol, are preferred because of the sorbitan ester solubility and ease of removal.

The impurity-containing (polyol-containing) sorbitan ester is first dissolved in a solution of a hydrocarbon and an polar organic solvent to produce a sorbitan ester solution. Lower boiling solvents such as hydrocarbons and polar organic solvents with less than about 10 carbon atoms are preferred for ease of removal of the solvents after treatment. The solution preferably contains hydrocarbon and polar organic solvent, preferably in a ratio within the range of about 1:1000 to about 5:1, more preferably about 1:100 to about 3:1, most preferably about 1:10 to about 2:1.

The sorbitan ester solution is then mixed or contacted with an aqueous metal salt solution. The salt solution contains water and from about 1 to about 20 weight percent, preferably, from about 5 to about 10 weight percent, based on the metal salt solution, of a metal salt. Suitable metal salts include, for example, metal halide salts, metal nitrate salts, metal acetate salts and metal sulfate salts. The preferred metal salt is a metal halide salt. The metal salt solution can optionally contain alcohols.

Suitable metal halide salts include, for example, alkali metal halides, alkaline earth metal halides, and trivalent metal halides. Examples of such halide salts include, for example LiCl, NaBr, KI, CaBr$_2$, MgI$_2$, NaCl, KCl, CaCl$_2$, MgCl$_2$, AlCl$_3$ and FeCl$_3$. The preferred metal halide salts are alkali metal halides and alkaline earth metal halides, particularly, NaCl, KCl, CaCl$_2$ and MgCl$_2$. Suitable sulfate salts are alkali metal sulfates, alkaline earth metal sulfates, and trivalent metal sulfates. Examples of such sulfate salts includes, for example, sodium sulfate, calcium sulfate, aluminum sulfate and ferric sulfate. Suitable acetate salts are alkali metal acetates, alkaline earth metal acetates, and trivalent metal acetates. Examples of such acetate salts includes, for example, sodium acetate, lithium acetate, magnesium acetate and aluminum acetate. Suitable nitrate salts are alkali metal nitrates, alkaline earth metal nitrates, and trivalent metal nitrates. Examples of such nitrate salts includes, for example, sodium nitrate, calcium nitrate, aluminum nitrate and ferric nitrate.

For convenience, the inventive process will further be described in terms of its preferred embodiment, in which a metal halide salt solution is used. In a typical process, the metal halide salt solution is added and mixed into the sorbitan ester solution to produce a combined solution. The ratio of the sorbitan ester solution to the metal halide salt solution is preferably within the range of about 10:1 to about 1:10, more preferably about 5:1 to about 1:5. Then, the combined solution is allowed to phase separate into an organic phase containing the hydrocarbon, the polar organic solvent and sorbitan ester and an aqueous phase containing water, metal halide salt and polyol impurities. The metal halide salt solution is preferably heated to a temperature within the range of about 25° C. to about 90° C,. more preferably about 45° C. to about 80° C,. with the upper limit below about the boiling point of the organic solvents used. For a hexane/isopropanol solution, the metal halide salt solution is preferably heated at a temperature within the range of about 50° C. to about 55° C,. to hasten the phase separation. Subsequently, the aqueous phase is separated from the organic phase and then the purified sorbitan ester is recovered by removing the organic solvents by flashing, distilling or other means for removing the organic solvents including hydrocarbons and the polar organic solvents. At least a portion of the separated aqueous phase can be recycled to the mixing stage and used for the further removal of polyol impurities.

Any of the known methods in the art to separate organic/aqueous liquid phases can be utilized in the invention. The mixing and the phase separation steps can be carried out in either a single vessel or multiple vessels. For example, the steps may be conducted in one agitated vessel or other suitable mixing device, and phase separation can be carried out in separate gravity settling vessel or other suitable mechanical separation device. These steps also can be repeated in multiple stages either batch or continuous mode. For example, multiple stage mixer-settlers, gravity extraction column, centrifugal extractor or other device known to those skilled in the art.

In another embodiment, the sorbitan ester solution can be contacted with the metal salt solution to remove the polyol impurities. In the inventive process, the polyols can be substantially extracted (at least about 60%, preferably at least about 70%, more preferably at least about 90%) into the metal salt solution.

For example, the polyols can be extracted by contacting the sorbitan ester solution with the metal salt solution in a liquid-liquid two-phase contactor such as described in U.S. Pat. No. 3,351,434, the disclosure of which is herein incorporated by reference. In general, the sorbitan ester solution and the metal salt solutions are pumped through a two-phase contactor tank in their different strata. The polyol impurities will be transferred to the metal salt solution when a disk wettable by the sorbitan ester solution rotates between the two solution layers. The disk is such that it is only wettable by the sorbitan ester solution. The treated-sorbitan esters are recovered from the treated-sorbitan ester solution.

The sorbitan ester solution can also be contacted with the metal salt solution to remove the polyol impurities by a dispersion-free solvent extraction method such as, for example, by a FIBER-FILM TM contactor (from Merichem Company) and hollow-fiber membrane technology. The FIBER-FILM TM contactor is described in U.S. Pat. Nos. 3,754,377; 3,758,404; and 3,839,487, the disclosure of which is herein incorporated by reference. In general, the aqueous metal salt solution is introduced onto the outside surface of continuous, small diameter fibers (e.g. glass fibers and metal fibers) placed inside a retained cylinder. The metal salt solution adheres to the fiber surface in preference to the sorbitan ester solution which flows through and parallel to the aqueous-wetted fiber material.

The hollow-fiber membrane techno is described in in U.S. Pat. Nos. 5,053,132; 4,997,569, 4,921,612 and 4,789,468, the disclosure of which is herein incorporated by reference. The hollow-fiber membrane technology is also described in Prasad, R. and Sirkar, K.K., "Dispersion-Free Solvent Extraction with Microporous Hollow-Fiber Modules," AIChE J., 34(2), 177 (1988). A hydrophilic microporous hollow-fiber module, a hydrophobic microporous hollow-fiber module or a membrane having both a hydrophilic side and a hydrophobic side can be used in the inventive process. In general, a hydrophilic microporous hollow-fiber module is preferred over a hydrophobic module because the solute distribution coefficient between organic and aqueous phases are less than 1. A hydrophilic microporous hollow-fiber module can be a regenerated cellulose hollow fiber or CUPROPHAN type hollow-fiber (from ENKA, FRG) for example. The two phases can be flowing concurrently or flowing in the opposite direction at either tube side or shell side. The aqueous phase flow (metal salt solution) can be tube side or shell side, but preferably shell side with the organic phase (sorbitan ester solution) kept at a pressure higher than the aqueous phase pressure to oppose the tendency of the aqueous phase which preferentially wets the hydrophilic membrane to flow through the membrane and disperse in the organic phase. Alternatively, an asymmetrically-wettable, porous membrane having a hydrophilic side and a hydrophobic side can be used for the extraction. These membranes can be a composite structure having a hydrophilic layer such as, for example, porous regenerated cellulose, porous cellulose-acetate, microporous glass and porous procelain and a hydrophobic layer such as, for example, porous polyethylene, porous polypropylene and porous polytetrafluoroethylene. The treated-sorbitan esters are recovered from the extracted-sorbitan ester solution.

The inventive process removes polyols while leaving the sorbitan esters undisturbed. Further, the inventive process is very efficient and effective in removing the polyols. Also, it has been found that the process of this invention has short phase separation time.

ILLUSTRATIVE EMBODIMENT

The following illustrative embodiments describe the process of the invention and are provided for illustrative purposes and are not meant as limiting the invention.

EXAMPLE 1

This example demonstrates purification of impurity-containing sorbitan esters according to the invention.

50 Milliliters of SPAN ® 20 emulsifying agent (sorbitan monolaurate from Imperial Chemical Industries, ICI) was dissolved in a mixture of 50 ml of hexanes and 50 ml of isopropyl alcohol. The solution was poured into a 250 ml separatory funnel and 50 ml of 10% wt. aqueous sodium chloride solution was added. The funnel was stoppered, shaken, then placed upright in a ring-stand to allow phase separation to occur. The salt solution was at ambient temperature. Total phase separation was complete in 10 minutes. The organic phase was collected and the organic solvent was flashed off. The recovered sorbitan monolaurate was analyzed by gas chromatography and compared to an identical sample of unwashed SPAN ® 20 emulsifying agent. The results are shown in Table 1. The results show a decrease in the amount of polyols present.

TABLE 1

| SAMPLE | Total ROH | Total FA** | Isosorbide*** | Sorbitan*** |
|---|---|---|---|---|
| unwashed | ND* | 2.58 | 7.34 | 5.99 |
| washed | ND | 2.67 | 0.19 | ND |

*ND denotes not detected, i.e., below detection limit of method at less than 0.05% wt or less than 0.3% wt for total ROH.
**FA denotes fatty acids, i.e., lauric acid.
***Polyols (condensed and unreacted)

EXAMPLE 2

This example demonstrates another embodiment of the inventive process.

50 Milliliters of SPAN ® 20 emulsifying agent (sorbitan monolaurate from ICI) was dissolved in a mixture of 50 ml of hexanes and 50 ml of isopropyl alcohol. The solution was poured into a 250 ml separatory funnel and 50 ml of 10% wt. aqueous sodium sulfate solution was added. The funnel was stoppered, shaken, then placed upright in a ring-stand to allow phase separation to occur. The salt solution was at ambient temperature. Total phase separation was complete in 8 minutes. The organic phase was collected and the organic solvent was flashed off. The recovered sorbitan monolaurate was analyzed by gas chromatography. The results are shown in Table 2.

EXAMPLE 3

This example demonstrates another embodiment of the inventive process.

The purification was carried out in a similar manner to Example 2 except petroleum ether (a low boiling fraction, 30°-60° C,. of petroleum consisting chiefly of hydrocarbons of the methane series, principally pentanes and hexanes from Baxter Co.) was substituted for hexanes. The phase separation was complete in 7.5 minutes. The results are shown in Table 2.

COMPARATIVE EXAMPLE 1

This example demonstrates a purification method where neat sorbitan monolaurate was washed with aqueous sodium sulfate solution.

50 Milliliters of SPAN ® 20 emulsifying agent (sorbitan monolaurate from ICI) was added to a 250 ml separatory funnel. 50 ml of a 10% wt. solution of aqueous sodium sulfate solution was added. The salt solution was at ambient temperature. The funnel was stoppered and shaken where upon a thick white emulsion formed. After 12 hours, approximately 30% phase separation had occurred. After 4 days approximately 60% phase separation had occurred. Total phase separation required 1-2 weeks. The results are shown in Table 2.

TABLE 2

| SAMPLE | TOTAL FA** | ISOSORBIDE** | SORBITAN** |
|---|---|---|---|
| Untreated SPAN ® 20 | 2.23 | 6.94 | 5.86 |
| Comparative Example 1 | 2.21 | 3.56 | 3.03 |
| Example 2 | 2.43 | 1.74 | 1.21 |
| Example 3 | 2.47 | 1.99 | 1.15 |

*FA denotes fatty acids.
**Polyols (condensed and unreacted)

EXAMPLE 4

This example demonstrates another embodiment of the inventive process.

Salt solutions of 10% wt. concentration were prepared for calcium chloride, sodium chloride and sodium sulfate. These salt solutions were kept at room temperature (25° C). Solutions of SPAN ® 20 emulsifying agent (sorbitan monolaurate from ICI) were prepared by dissolving 80 ml of the sorbitan ester in 200 ml of a 1:1 mixture of isopropanol and toluene. To each of 4 separatory funnels was added 50 ml of the SPAN ® 20 solution. Each of funnels were then charged with 50 ml of a salt wash solution. The fourth flask was charged with 50 ml of deionized water. Each funnel was then stoppered, shaken vigorously 15 seconds, vented, uprighted, then unstoppered. Bulk phase separation occurred most quickly for calcium chloride, in less than 10 minutes. Sodium chloride and sodium sulfate bulk separated within 15 minutes. The solution washed with deionized water did not separate after 1 week: incomplete separation was evident after 2 weeks.

EXAMPLE 5

This example demonstrates another embodiment of the inventive process.

Solutions of calcium chloride were prepared at 1, 3, 5 and 10% wt. concentration. These solutions were warmed to 50° C. by placing in an oven. 100 g of SPAN ® 20 emulsifying agent (sorbitan monolaurate from ICI) was dissolved in 270 g of a 1:1 solution of isopropanol and toluene. The concentration of the sorbitan ester was 27%. Four 125 ml separatory funnels were used, each was charged with 50 ml of the sorbitan ester solution. Additionally, each funnel was charged with the warmed salt solution, each at a different concentration. Each flask was stoppered and shaken vigorously for 1 minute, vented, then uprighted and unstoppered. Bulk phase separation occurred most quickly for the sample washed with 10% salt solution, less than 10 minutes. The other samples bulk phase separated in greater than 10 minutes, but less than 2 hours. Total separation occurred in less than 2 hours for all samples.

EXAMPLE 6

Timed experiments were conducted using 10% sodium chloride solutions and 33% SPAN ® 20 emulsifying agent solutions in 1:1 isopropanol:toluene.

150 Milliliters of the emulsifying agent solution was added to a 500 ml separatory funnel. 100 ml of the salt wash solution was added, either warmed at 60° C. or at room temperature (25° C.). The flask was stoppered, shaken vigorously 10 seconds, vented, uprighted and unstoppered. Bulk phase separation occurred in 5:00 minutes for salt wash at room temperature and 2:56 minutes for warmed salt solution.

EXAMPLE 7

The temperature effect on the inventive process is illustrated.

10 Percent by weight salt solutions of potassium chloride, sodium chloride, calcium chloride and sodium sulfate were prepared. Each salt solution was divided into two portions. One portion was warmed at 60° C. The other portion was kept at room temperature. A solution of SPAN ® 20 emulsifying agent was prepared by dissolving 200 ml of surfactant in 200 ml of isopropanol and 200 ml of toluene. The solution was stirred for 30 minutes to completely dissolve the material. To each of 4 separatory funnels was added a 50 ml charge of the surfactant solution. 50 ml of salt wash solution was then added. Each flask was stoppered, shaken vigorously for 10 seconds, vented, uprighted and then unstoppered. The time for bulk phase separation to occur was measured. The time was seen to vary with the temperature of the wash solution, faster bulk phase separation occurring when the salt wash solution was warmed. The results are shown in Table 3.

TABLE 3

| Salt Solution | Room Temperature | Warmed |
|---|---|---|
| NaCl | 1:40 (minutes:seconds) | 1:08 |
| KCl | 1:42 | 1:04 |
| CaCl$_2$ | 1:17 | 1:00 |
| NaSO$_4$ | 1:58 | 1:18 |

EXAMPLE 8

This example demonstrates further embodiments of the inventive process.

A 10% wt. solution of sodium chloride was warmed at 60° C. by placing in a warming oven. In a typical run, 20 ml of SPAN ® 20 emulsifying agent (sorbitan monolaurate from ICI) was dissolved in a mixture of 20 ml of isopropanol and 20 ml of a cosolvent. Cosolvents were hexane, petroleum ether, cyclohexane and hexadecane. The sorbitan ester solutions were placed in 250 ml separatory funnels. 50 ml of warmed salt solution was added to each funnel, which was then stoppered, shaken and vented. The funnels were uprighted, stopper removed, and the time for bulk phase separation to occur measured. Results are shown in Table 4 below.

TABLE 4

| Cosolvent | Time |
|---|---|
| hexane | 0:54 (minutes:seconds) |
| petroleum ether | 1:10 |
| cyclohexane | 1:19 |

TABLE 4-continued

| Cosolvent | Time |
|---|---|
| hexadecane | 12:00 |

EXAMPLE 9

This example demonstrates another embodiment of the inventive process.

In a vial, 5 ml of SPAN ® 20 emulsifying agent (sorbitan monolaurate from ICI) was dissolved in a mixture of 5 ml of hexane and 5 ml of the following organic solvents and shaken. The organic solvents were acetone, benzaldehyde, dioxane, tetrahydrofuran, ethyl acetate, pyridine, acetonitrile, methylene chloride, tetramethylene sulfone, and diethyl amine. 10 ml of 10% aqueous NaCl was then added and the vials were vigorously shaken. Phase separation for acetone, benzaldehyde dioxane, tetrahydrofuran, ethyl acetate, pyridine and acetonitrile occurred within 2-24 hours. Methylene chloride and tetramethylene sulfone did not phase separate readily. A chemical reaction occurred with diethyl amine.

EXAMPLE 10

This example demonstrates another embodiment of the inventive process.

A 10% wt. solution of aluminum sulfate, ferric chloride and ferric nitrate was prepared. An sorbitan ester solution was prepared by dissolving 50 ml of SPAN ® 20 emulsifying agent (sorbitan monolaurate from ICI) in 50 ml of isopropanol and 50 ml of hexane. The mixture was stirred to give a homogenous solution The solution of aluminum sulfate, ferric chloride and ferric nitrate were each placed in a 250 ml separatory funnel. 50 ml of the sorbitan ester solution was also placed in each of the three 250 ml separatory funnels. The funnels were stoppered, shaken, vented, then uprighted to allow phase separation to occur. For each solution, phase separation occurred within 10 minutes. For ferric chloride and ferric nitrate solutions, the salt solutions were orange.

EXAMPLE 11

This example demonstrates another embodiment of the inventive process.

SPAN ® 20 emulsifying agent (sorbitan monolaurate from ICI) was dissolved in mixtures of isopropanol-(IPA)/hexane in various ratios:

| | Combination | Ratio | SPAN ® 20 (ml) |
|---|---|---|---|
| 1. | 5 ml IPA/25 ml hexane | 1:5 | 30 |
| 2. | 5 ml IPA/50 ml hexane | 1:10 | 55 |
| 3. | 25 ml IPA/5 ml hexane | 5:1 | 30 |
| 4. | 50 ml IPA/5 ml hexane | 10:1 | 55 |

The above combinations were stirred to homogeneous solutions. 1 and 2 gave cloudy pale yellow liquids. 2 was almost opaque. 4 was transparent. The contents of each flask was poured into each of 4 separatory funnels. To 1 and 3 was added 30 ml of 10% aqueous calcium chloride. To 2 and 4 was added 55 ml of the same. Each flask was stoppered, shaken, vented then uprighted to allow phase separation to occur.

Phase separation for 3 and 4 was rapid, within 5 minutes. Phase separation for 1 and 2 was much slower, required 18 hours or more. The water used in the wash step was recovered to determine if IPA dissolved in it.

Based on these results, it appears that IPA does not significantly dissolve in the salt aqueous phase.

| #3 | 30 ml wash used | 30 ml recovered |
|---|---|---|
| #4 | 55 ml wash used | ~60 ml recovered |

The aqueous layers of 1 and 2 remained thick and milky after 18 hours. When recovered, these layers were much greater in volume than the amount used in the wash. It appears that phase separation was not complete after 18 hours, and organic phase was emulsified in the wash phase.

EXAMPLE 12

This example demonstrates another embodiment of the inventive process.

A solution of SPAN ® 20 emulsifying agent (sorbitan monolaurate from ICI) was prepared by dissolving 150 ml of SpAN ® 20 emulsifying agent in 150 ml hexane and 150 ml isopropanol. The mixture was stirred until the solution was homogeneous. The resulting solution was washed with 10% aqueous solution of sodium sulfate.

1. aqueous:organic:10:1

Ten parts of aqueous phase was used to wash 1 part of the SPAN ® 20 solution. Phase separation occurred overnight, approximately 18 hours. Phases were clear after this time.

2 aqueous:organic:1:1

1 part aqueous phase was used to wash 1 part of the SPAN ® 20 solution. Phase separation was complete in 1 minute, 15 seconds.

3. aqueous:organic:1:10

1 part of aqueous phase was used to wash 10 parts of the SPAN ® 20 solution. The water phase disappeared, apparently dissolving up into the organic phase. Salt crystals formed and adhered to the sides of the separatory funnel.

We claim:

1. A process for removing polyols from a polyol-containing sorbitan ester mixture comprising the steps of:
   a) dissolving the polyol-containing sorbitan ester mixture in a solution comprising at least one hydrocarbon and a polar organic solvent wherein the ratio of said hydrocarbon to said organic solvent is within the range of about 1:1000 to about 5:1, to produce a sorbitan ester solution;
   b) adding and mixing into the sorbitan ester solution, a metal salt solution comprising water and from about 1 to about 20 weight percent, based on the salt solution, of a metal salt selected from the group consisting of halides, nitrates, acetates and sulfates of alkali metals, alkaline earth metals, and trivalent metals to produce a combined solution;
   c) phase separating the combined solution into an organic phase comprising the hydrocarbon, polar organic solvent and sorbitan ester and an aqueous phase comprising water, metal salt and polyol;
   d) separating the aqueous phase from the organic phase; and
   e) then recovering the thus-treated sorbitan ester from the organic solution.

2. The process of claim 1 wherein the salt solution is heated to a temperature within the range of about 20° C. to about 90° C. prior to step b).

3. The process of claim 1 wherein the hydrocarbon is selected from the group consisting of $C_{5-20}$ alkanes, $C_{5-20}$ cycloalkanes, $C_{6-20}$ aromatics.

4. The process of claim 3 wherein the metal salt is selected from the group consisting of alkali metal halides, alkaline earth metal halides and trivalent metal halides.

5. The process of claim 4 wherein the metal salt is selected from the group consisting of alkali metal halides and alkaline earth metal halides.

6. The process of claim 5 wherein the hydrocarbon is selected from the group consisting of pentane, hexane, heptane, octane, decane, hexadecane, cyclohexane, toluene, ethyl benzene, and petroleum ether.

7. The process of claim 6 wherein the metal halide salt is selected from the group consisting of LiCl, NaBr, KI, $CaBr_2$, $MgI_2$, NaCl, KCl, $CaCl_2$ and $MgCl_2$.

8. The process of claim 7 wherein the metal halide salt is present in an amount of about 5 to 10 weight percent based on the salt solution.

9. The process of claim 8 wherein the metal halide salt is selected from the group consisting of NaCl, KCl, $CaCl_2$ and $MgCl_2$.

10. The process of claim 9 wherein the ratio of the sorbitan ester solution to the metal salt solution is within the range of about 10:1 to about 1:10.

11. The process of claim 10 wherein the polar organic solvent is selected from the group consisting of oxygenated hydrocarbons, nitrogen bases having a pKa value for their conjugate acids of less than about 10 and inert sulfur-containing solvents.

12. The process of claim 11 wherein the polar organic solvent is selected from the group consisting of $C_1$–$C_{11}$ alcohols, aldehydes, ketones, esters and ethers.

13. The process of claim 12 wherein the organic solvent is an alcohol.

14. The process of claim 13 wherein the alcohol is selected from the group consisting of methanol, ethanol, n-propanol, isopropanol, butanol, pentanol, hexanol, cyclohexanol, benzyl alcohol and decanol.

15. The process of claim 14 wherein the alcohol is a $C_1$–$C_5$ alcohol.

16. The process of claim 15 wherein the hydrocarbon is pentane or hexane.

17. A process for removing polyols from a polyol-containing sorbitan ester mixture comprising the steps of:
   a) dissolving the polyol-containing sorbitan ester mixture in a solution comprising at least one hydrocarbon and a polar organic solvent wherein the ratio of said hydrocarbon to said organic solvent is within the range of about 1:1000 to about 5:1, to produce a sorbitan ester solution;
   b) providing a metal slat solution comprising water and from about 1 to about 20 weight percent, based on the salt solution, of a metal salt selected from the group consisting of halides, nitrates, acetates and sulfates of alkali metals, alkaline earth metals, and trivalent metals;
   c) contacting the sorbitan ester solution and metal salt solution under conditions effective to extract the polyols from the sorbitan ester solution into the metal salt solution;
   d) separating the thus treated-sorbitan ester solution and the metal salt solution; and
   e) then recovering the sorbitan ester from the separated-sorbitan ester solution.

18. The process of claim 17 in which the sorbitan ester solution is contacted with the metal salt solution in a liquid-liquid two-phase contactor.

19. The process of claim 17 in which the sorbitan ester solution is contacted with the metal salt solution in a FIBER-FILM contactor.

20. The process of claim 17 in which the sorbitan ester solution is contacted with the metal salt solution through a hollow-fiber membrane.